United States Patent

Hurt

[11] 4,147,781
[45] Apr. 3, 1979

[54] O,S-DIALKYL O-BENZAMIDOPHENYL PHOSPHOROTHIOLATES AND PHOSPHORODITHIOATES AND PESTICIDAL METHODS

[75] Inventor: William S. Hurt, Collegeville, Pa.

[73] Assignee: Rohm and Haas Company, Philadelphia, Pa.

[21] Appl. No.: 854,929

[22] Filed: Nov. 25, 1977

[51] Int. Cl.² ............... A01N 9/36; C07F 9/165
[52] U.S. Cl. ......................... 424/211; 260/944
[58] Field of Search ............... 260/944; 424/211

[56] References Cited

U.S. PATENT DOCUMENTS 3,855,362  12/1974  Drabek et al. ............ 260/944 OR

Primary Examiner—Anton H. Sutto
Attorney, Agent, or Firm—Susan Borden-Evans

[57] ABSTRACT

This invention relates to novel organophosphorothiolates and phosphorodithioates of the formula:

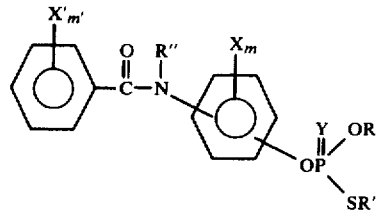

wherein in R is a $(C_1-C_4)$alkyl group;
R' is a $(C_3-C_6)$alkyl group;
R" is a hydrogen atom, or a $(C_1-C_5)$alkyl group;
X is a halogen atom, a $(C_1-C_5)$alkyl group, or a $(C_1-C_5)$alkoxy group;
X' is a halogen atom, a nitro group, a cyano group, a $(C_1-C_5)$alkyl group, a $(C_1-C_5)$alkoxy group, or a $(C_1-C_5)$alkylthio group;
Y is an oxygen atom or a sulfur atom; and m and m' are independently integers from 0 to 3; to compositions containing them and to methods of using them to control pests.

18 Claims, No Drawings

O,S-DIALKYL O-BENZAMIDOPHENYL PHOSPHOROTHIOLATES AND PHOSPHORODITHIOATES AND PESTICIDAL METHODS

This invention relates to novel organophosphorothiolates and phosphorodithioates, to compositions containing them, to methods of using them to control a variety of harmful pests and to methods of preparing them. In addition to possessing outstanding pesticidal activity, compounds of the present invention exhibit such desirable characteristics as activity against organophosphorus resistant species, residual activity, low toxicity to warm-blooded animals and low phytotoxicity for economically important plant species.

The novel compounds of this invention can be represented by the formula:

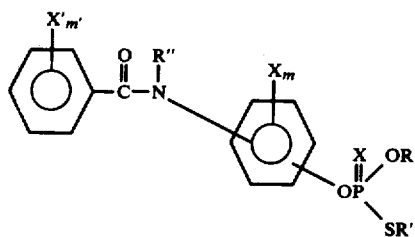 (I)

wherein
R is a $(C_1-C_4)$alkyl group, preferably a $(C_1-C_3)$-alkyl group, more preferably methyl or ethyl, most preferably ethyl;
R' is a $(C_3-C_6)$alkyl group, preferably a $(C_3-C_5)$alkyl group of the formula

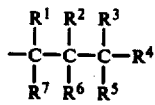

wherein
$R^1-R^7$ are individually hydrogen, methyl or ethyl; more preferably $(C_3-C_4)$alkyl, most preferably n-propyl, s-butyl or isobutyl;
R" is a hydrogen atom, or a $(C_1-C_5)$alkyl group, preferably a $(C_1-C_3)$alkyl group, most preferably a methyl group;
X is a halogen atom, preferably chlorine; a $(C_1-C_5)$-alkyl group, preferably a $(C_1-C_3)$alkyl group, most preferably a methyl or ethyl group; or a $(C_1-C_5)$-alkoxy group, preferably a $(C_1-C_3)$alkoxy group, most preferably a methoxy or ethoxy group;
X' is a halogen atom, preferably chlorine; a nitro group, a cyano group, a $(C_1-C_5)$alkyl group, preferably a $(C_1-C_3)$alkyl group, most preferably a methyl group; a $(C_1-C_5)$alkoxy group, preferably a $(C_1-C_3)$alkoxy group, most preferably a methoxy group; or a $(C_1-C_5)$alkylthio group, preferably a $(C_1-C_3)$alkylthio group, most preferably a methylthio group;
Y is an oxygen atom or a sulfur atom, preferably an oxygen atom;
m is an integer from 0 to 3; and
m' is an integer from 0 to 3, preferably from 0 to 1.

As used in the specification and claims, the terms "alkyl", "alkoxy", and "alkylthio", are intended to include branched chain as well as straight chain groups. Representative groups include, for example, methyl, ethyl, n-propyl, sec-butyl, isobutyl, pentyl, neopentyl, 2-methylpentyl, n-hexyl, methoxy, ethoxy, propoxy, sec-butoxy, pentoxy, methylthio, ethylthio, isopropylthio, n-propylthio, isobutylthio, tert-butylthio, pentylthio, and the like.

The organophosphorothiolates and phosphorodithioates described above can exist in their isomeric forms, wherein the φCONR" group of Formula I is attached to the aryl ring in a position which is ortho, meta or para, preferably ortho, to the phosphorothiolate or phosphorodithioate group.

The preferred compounds of this invention, i.e. those having especially enhanced acaricidal, insecticidal, and nematocidal activity, can be represented by Formula I wherein R is an ethyl group; R' is an n-propyl group, an isobutyl group, or a sec-butyl group; R" is a hydrogen atom; m is the integer 0; X' is a chlorine atom; Y is an oxygen atom; and m' is an integer of 0 or 1.

Typical examples of compounds within the scope of this invention include but are not limited to the following:

O-[2-(benzamido)phenyl] O-methyl S-n-propyl phosphorothiolate
O-[2-(3',5'-dichlorobenzamido)phenyl] O-ethyl S-n-propyl phosphorothiolate
O-[3-(4'-bromobenzamido)phenyl] O-ethyl S-n-propyl phosphorothiolate
O-[3-(4'-cyanobenzamido)phenyl] O-ethyl S-n-propyl phosphorothiolate
O-[3-methyl-4-(4'nitrobenzamido)phenyl] O-ethyl S-n-propyl phosphorothiolate
O-[2,6-dichloro-4-(4'fluorobenzamido)phenyl] O-ethyl S-n-propyl; phosphorothiolate
O-[3-methyl-4-(4'-methylthiobenzamido)phenyl] O-ethyl S-n-propyl phosphorodithioate
S-sec-butyl O-ethyl O-[2-(4'methylbenzamido)phenyl] phosphorothiolate
S-n-butyl O-ethyl O-[3-(4'-methoxybenzamido)phenyl] phosphorothiolate
O-[2-(benzamido)phenyl] O-ethyl S-n-propyl phosphorodithioate
O-ethyl S-n-pentyl O-[4-(N-n-propylbenzamido)phenyl] phosphorodithioate
O-[2-(4'-t-butylbenzamido)4-butoxyphenyl] O-S-isobutyl phosphorodithioate
O-[2-(4'-pentylthiobenzamido)phenyl] O,S-di-n-propyl phosphorothiolate
O-[2-(4'-t-butoxybenzamido)-4-t-butylphenyl] O-ethyl S-n-propyl phosphorothiolate
O-[2-(2',4',6'-trichlorobenzamido)-4-methoxyphenyl] O-ethyl S-isobutyl phosphorothiolate The compounds of this invention can be prepared by a variety of methods known per se for analogous compounds. One method involves reacting a phenol with an O,S-dialkylphosphorochloridothiolate or phosphorochloridodithioate. The general reaction can be represented by the following equation:

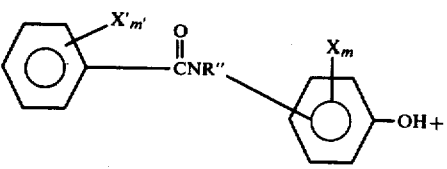

-continued

wherein R, R', R", X, X', Y, m, and m' are as defined for Formula I. One method for preparing phenolic starting material is shown in Example 17, page 10.

An acid acceptor such as a tertiary amine or an alkali carbonate or hydroxide can be employed as a scavenger in this preparation. Representative acid acceptors include pyridine, trimethylamine, triethylamine, dimethylaniline, lithium carbonate, sodium hydroxide, potassium hydroxide, and the like. Generally a substantially equimolar ratio of reactants is preferred but an excess of any of the reactants can be employed. While not required, the reaction is advantageously carried out in the presence of an inert organic solvent such as an ether, aromatic hydrocarbon, halogenated aromatic hydrocarbon, aliphatic hydrocarbon, aliphatic ketone, aliphatic nitrile, and the like. Suitable solvents include benzene, toluene, heptane, methylethyl ketone, acetone, ethyl ether, acetonitrile and dioxane. The reaction is generally conducted in a temperature range of about $-10°$ to about 100° C. or more, and preferably in the range of about 0° to about 60° C.

In addition to the above procedure, the compounds of this invention can be prepared by reacting an alkali phenoxide with an O,S-dialkylphosphorochloridothiolate or phosphorochloridodithioate. This reaction can be represented by the following equation:

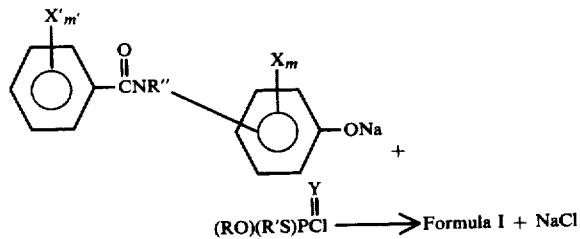

wherein R, R', R", X, X', Y, m and m' are as defined for Formula I.

Reaction conditions, including choice of solvents, temperature, and molar ratios correspond to the conditions described above for the reaction of an O,S-dialkylphosphorochloridothiolate or phosphorochloridodithioate with a phenol except that there is no need to employ an acid acceptor in this reaction.

All of the starting materials used in the preparation of the compounds of this invention are known compounds or are readily prepared by adaptations of known methods of preparation.

The following examples are given by way of illustration, and are not to be considered as limitations of the present invention. Specific preparative examples of the compounds of Examples 1 to 3 are provided. Table I lists physical data for a number of representative compounds of the invention. In the examples, all temperatures are in degrees Celsius and parts and percentages are by weight unless otherwise indicated.

EXAMPLE 1

O-[4-(denzamido)phenyl] O-ethyl S-n-propyl phosphorothiolate

To a slurry of 6.4 g (0.03 mole) of 4-(benzamido)-phenol in 300 ml of acetonitrile is added a dispersion of 0.77 g. (0.032 mole) of sodium hydride in 30 ml of acetonitrile at 50° C. The slurry is held at 55°–65° C. for 40 minutes to complete the formation of the sodium salt and then cooled to 26° C. The O-ethyl S-n-propyl phosphorochloridothiolate (7.0 g., 0.033 mole) is then added dropwise over a 3 minute period. The slurry is stirred overnight at 40° C. and then filtered to remove sodium chloride. The filtrate is concentrated in vacuo to give 12.0 g. (105%) of the crude phosphorothiolate as a red amber oil. The oil is purified by chromatographing on silicic acid using butyl acetate:heptane as the eluent to give 7.8 g. (68%) of the phosphorothiolate as a pale amber oil which crystallizes on standing, m.p. = 72°–74° C. (ethyl acetate-hexane). Anal. calc. (found) for $C_{18}H_{22}NO_4PS$: C 57.0 (57.2); H 5.85 (5.90); N 3.69 (3.94).

EXAMPLE 2

O-[3-(4'-chlorobenzamido)phenyl] O-ethyl S-n-propyl phosphorothiolate

To a yellow solution of 7.42 g. (0.03 mole) of 3-(4'-chlorobenzamide)phenol in 150 ml of 1,2-dimethoxyethane is added in portions 1.68 g. (0.04 mole) of sodim hydride (57% dispersion in mineral oil) at 35° C. After stirring an additional 5 minutes, 6.08 g. (0.03 mole) of O-ethyl S-n-propyl phosphorochloridothiolate is added in portions as the solution mildly exotherms (+5° C.). The solution is held for 2 days at room temperature and then worked up and purified in a manner similar to Example 1 to give the phosphorothiolate as an oil.

Anal. calc. (found) for $C_{18}H_{21}ClNO_4PS$: C 52.2 (52.1); H 5.07 (5.29); Cl 8.57 (8.51); N 3.38 (3.62).

EXAMPLE 3

O-[2-(benzamido)phenyl] O-ethyl S-n-propyl phosphorothiolate

A solution of 5.7 g. (0.028 mole) of O-ethyl S-n-propyl phosphorochloridothiolate in 50 ml. of benzene is added dropwise to a stirring suspension of 6.0 g. (0.0282 mole) of 2-(benzamido)phenol and 3.8 g. (0.0375 mole) of triethyl amine in 150 ml of benzene at 25°–34° C. The mixture is warmed to 60° C. for three hours and then cooled to room temperature and filtered to remove triethylamine hydrochloride. The filtrate is washed once with 200 ml of aqueous sodium bicarbonate, twice with 200 ml portions of water and then concentrated in vacuo to give 9.4 g. (88%) (of the phosphorothiolate as a yellow oil. The oil is purified by chromatographing on silica gel using 70:25:5 hexane:benzene:isopropanol as the eluent.

Anal. calc. (found) for $C_{18}H_{22}NO_4PS$: C 57.0 (56.6); H 5.8 (5.8); N 3.4 (3.5).

EXAMPLES 4 - 16

Similarly are prepared
(4) O-[4-(4'chlorobenzamido)phenyl] O-ethyl S-n-propyl phosphorothiolate
(5) S-sec-butyl O-[4-(4'-chlorobenzamido)phenyl] O-ethyl phosphorothiolate
(6) O-[4-(4'-chlorobenzamido)phenyl] O-ethyl S-isobutyl phosphorothiolate
(7) S-n-butyl O-[4-(4'-chlorobenzamido)phenyl] O-ethyl phosphorothiolate
(8) O-[4-(2'chlorobenzamido)phenyl] O-ethyl S-n-propyl phosphorothiolate
(9) O-ethyl O-[4-(4'-nitrobenzamido)phenyl] S-n-propyl phosphorothiolate

(10) O-[3-(benzamido)phenyl] O-ethyl S-n-propyl phosphorothiolate
(11) O-[3-(benzamido)phenyl] S-sec-butyl O-ethyl phosphorothiolate
(12) O-[2-(benzamido)phenyl] S-sec-butyl O-ethyl phosphorothiolate
(13) O-[2-(benzamido)phenyl] O-ethyl S-isobutyl phosphorothiolate
(14) O-[2-(4'-chlorobenzamido)phenyl] O-ethyl S-n-propyl phosphorothiolate
(15) O-[4-(benzamido)phenyl] S-sec-butyl O-ethyl phosphorothiolate
(16) O-ethyl O-[4-(N-methylbenzamido)phenyl] S-n-propyl phosphorothiolate

EXAMPLE 17

2-(4-chlorobenzamido)phenol

This example shows a typical method for preparing phenols useful in synthesizing the compounds of the invention.

A solution of p-chlorobenzoyl chloride (35 g., 0.2 mole) in 25 ml of dimethoxyethane is added dropwise at 25° to a dispersion of o-aminophenol (43.6 g., 0.4 mole) in 300 ml of dimethoxyethane. There is a 20° exotherm and a color change from brown to red. When the addition is complete, the mixture is heated to 50° for two hours, then the solvent is evaporated in vacuo to half volume. The residue is poured over 200 g of ice, and the product is collected by vaccum filtration.

The recovered precipitate is slurred with 300 ml of hot ethyl acetate, refiltered, dried at 25°/0.7 mm to 34.5 g of bright yellow solid, m.p. 171°–3°.

TABLE I
Elemental Analysis

| Example No. | X | R' | Pos. | Empirical Formula | M.P. °C. | Element | Found | Calc. |
|---|---|---|---|---|---|---|---|---|
| 1 | H | Pr-n | 4 | $C_{18}H_{22}NO_4PS$ | 72–74 | C | 57.2 | 57.0 |
|   |   |   |   |   |   | H | 5.9 | 5.8 |
|   |   |   |   |   |   | N | 3.9 | 3.7 |
| 2 | 4-Cl | Pr-n | 3 | $C_{18}H_{21}ClNO_4PS$ | oil | C | 52.1 | 52.2 |
|   |   |   |   |   |   | H | 5.3 | 5.1 |
|   |   |   |   |   |   | N | 3.6 | 3.4 |
|   |   |   |   |   |   | Cl | 8.5 | 8.6 |
| 3 | H | Pr-n | 2 | $C_{18}H_{22}NO_4PS$ | oil | C | 56.5 | 57.0 |
|   |   |   |   |   |   | H | 5.8 | 5.8 |
|   |   |   |   |   |   | N | 3.5 | 3.7 |
| 4 | 4-Cl | Pr-n | 4 | $C_{18}H_{21}ClNO_4PS$ | oil | C | 52.4 | 52.3 |
|   |   |   |   |   |   | H | 5.5 | 5.1 |
|   |   |   |   |   |   | N | 2.8 | 3.4 |
| 5 | 4-Cl | Bu-s | 4 | $C_{19}H_{23}ClNO_4PS$ | 86.5–88 | C | 53.2 | 53.3 |
|   |   |   |   |   |   | H | 5.4 | 5.4 |
|   |   |   |   |   |   | Cl | 8.3 | 8.3 |
| 6 | 4-Cl | Bu-i | 4 | $C_{19}H_{23}ClNO_4PS$ | 81–82.5 | C | 53.4 | 53.3 |
|   |   |   |   |   |   | H | 5.4 | 5.4 |
|   |   |   |   |   |   | Cl | 8.1 | 8.3 |
| 7 | 4-Cl | Bu-n | 4 | $C_{19}H_{23}ClNO_4PS$ | 79–83 | C | 52.9 | 53.3 |
|   |   |   |   |   |   | H | 5.4 | 5.4 |
|   |   |   |   |   |   | Cl | 8.1 | 8.3 |
| 8 | 2-Cl | Pr-n | 4 | $C_{18}H_{21}ClNO_4PS$ | 80–82 | C | 52.5 | 52.2 |
|   |   |   |   |   |   | H | 4.9 | 5.1 |
|   |   |   |   |   |   | Cl | 8.7 | 8.6 |
| 9 | 4-NO$_2$ | Pr-n | 4 | $C_{18}H_{21}N_2O_6PS$ | 92–94 | C | 50.6 | 50.9 |
|   |   |   |   |   |   | H | 4.9 | 4.9 |
|   |   |   |   |   |   | N | 6.7 | 6.6 |
| 10 | H | Pr-n | 3 | $C_{18}H_{22}NO_4PS$ | oil | C | 57.8 | 57.0 |
|   |   |   |   |   |   | H | 6.0 | 5.8 |
|   |   |   |   |   |   | N | 3.9 | 3.7 |
| 11 | H | Bu-s | 3 | $C_{19}H_{24}NO_4PS$ | oil | C | 57.6 | 58.0 |
|   |   |   |   |   |   | H | 6.5 | 6.1 |
|   |   |   |   |   |   | N | 4.0 | 3.6 |
| 12 | H | Bu-s | 2 | $C_{19}H_{24}NO_4PS$ | oil | C | 57.5 | 58.0 |
|   |   |   |   |   |   | H | 6.2 | 6.1 |
|   |   |   |   |   |   | N | 3.8 | 3.6 |
| 13 | H | Bu-i | 2 | $C_{19}H_{24}NO_4PS$ | oil | C | 56.9 | 58.0 |
|   |   |   |   |   |   | H | 6.3 | 6.1 |
|   |   |   |   |   |   | N | 3.7 | 3.6 |
| 14 | 4-Cl | Pr-n | 2 | $C_{18}H_2ClNO_4PS$ | oil | C | 51.8 | 52.2 |
|   |   |   |   |   |   | H | 5.0 | 5.1 |
|   |   |   |   |   |   | N | 3.6 | 3.4 |
| 15 | H | Bu-s | 4 | $C_{19}H_{24}NO_4PS$ | 86–88 | C | 58.2 | 58.0 |
|   |   |   |   |   |   | H | 6.2 | 6.1 |
|   |   |   |   |   |   | Cl | 3.8 | 3.6 |
| 16 | H | Pr-n | 4 | $C_{19}H_{24}NO_4PS$ | oil | C | 57.1 | 58.0 |
|   |   |   |   |   |   | H | 6.5 | 6.1 |

TABLE I-continued

Elemental Analysis

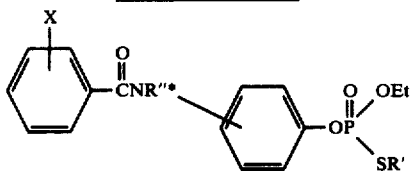

| Example No. | X | R' | Pos. | Empirical Formula | M.P. °C. | Element | Found | Calc. |
|---|---|---|---|---|---|---|---|---|
| | | | | | | N | 3.7 | 3.6 |

*R" = CH₃ for example 16; H for all other examples.

The compounds of this invention are useful for the protection of plants and animals from the ravages of harmful and annoying pests. These compounds are particularly effective against nematodes and arthropods (in varying stages of development). As arthropodicides, the compounds of this invention are especially effective against members of the Class Arachnoidea, which includes the Order Acarina, as represented by mites and ticks, and the Class Insecta, the insects. Among the nematodes and arthropods which are effectively controlled by the compounds of the present invention are soil nematodes, e.g. the southern root knot nematode (*Meloidogyne incognita*), the chewing insects, e.g. the southern armyworm (*Spodoptera eridania*), the sucking insects, e.g. the green peach aphid (*Myzus persicae*), soil-dwelling insects, e.g. the southern corn rootworm (*Diabrotica undecimpunctata howardi*), houseflies, (*Musca domestica*), mites, e.g. the two-spotted spider mite (*Tetranychus urticae*), and others.

Certain compounds of this invention are also active vs plant pathogens, e.g. vs phytopathogenic fungi. Some of the plant diseases controlled by compounds of this invention include, for example, wheat leaf rust (*Puccinia recondita*), bean powdery mildew (*Erysiphe polygoni*), grape downy mildew (*Plasmopora viticola*), rice blast (*Piricularia oryzae*) and the like.

Generally, control of pests is achieved in accordance with this invention by application of the compounds of this invention in pesticidally effective amounts either directly to the pests to be controlled or to the loci to be protected from attack by such pests. For example, food, fiber, forage, forest, and ornamental crops and stored products thereof would represent plant protection loci. Treatment with the compounds of this invention of domestic animals, and their immediate environs similarly constitute representative loci for protection against various annoying ectoparasitic or endoparasitic Acarina (Acari) and Insecta. Accordingly, compounds of the present invention provide utility as the essential active ingredient of pesticidal compositions suitable for agricultural and sanitary purposes.

The term "control" as employed in the specification and claims of this application is to be construed as any means which adversely affects the existence or growth of any living organism. Such means can comprise a complete killing action, eradication, arresting in growth, repulsion, inhibition, reduction in number, or any combination thereof.

Initial evaluations are made on the following mite, insect and nematode species:

| Code Symbol | Common Name | Latin Name |
|---|---|---|
| TSM | Two-spotted spider mite | *Tetranychus urticae* |
| SAW | Southern Armyworm | *Spodoptera eridania* |
| Nema | Southern root-knot-nematode | *Meloidogyne incognita* |

A test solution containing 600 ppm of test compound is made by dissolving the test compound in a solvent (acetone: methanol, 1:1), adding surfactant and then water to give an acetone:methanol:water system of 10:10:80. A 1:1 mixture of an alkylarylpolyetheralcohol (commercially available under the trademark Triton ® X-155) and a modified phthalic glycerol alkyd resin (commercially available under the trademark Triton ® B-1956 ®) is utilized at the equivalent of one ounce per 100 gallons of test solution as a surfactant.

For the mite test, infested bean (*Phaseolus limeanus*) leaf sections (~1×1 inches) containing about 50 mites are placed in a Petri dish lid on a moistened piece of cotton. The leaves are then sprayed with the test solution using a rotating turntable. They are held for 24 hours and then the percent kill is determined.

For the armyworm test, detached bean leaves on pieces of moistened filter paper are sprayed as above for the mite test in similar dishes and allowed to dry. One such dish is infested with 10 third instar southern armyworm larvae. The dish is covered. After holding for 48 hours, the percent kill is obtained.

For the nematode test, soil is homogeneously inoculated with a macerated blend of tomato roots heavily knotted with the root knot nematode. Ten milliliters of the test solution are added to 200 milliliters of the inoculated soil in a 16 oz. jar to give a concentration by volume of about 30 ppm. The jar is shaken to insure thorough mixing, immediately uncapped, and allowed to air for 24 hours. The soil is then placed into a 3-inch plastic pot after which time 3 cucumber (*Cucumis sativus*) seeds are planted. After 23 days thereafter, the cucumber plants are removed from the soil and root system examined for the presence of knots. A total of 25 knots or less is considered as a measure of control.

Table II gives the results of the foregoing biological evaluations.

TABLE II

| | Pesticidal[a] Activity | | |
|---|---|---|---|
| Compound | TSM[b] | SAW[b] | Nema[c] |
| 1 | 100 | 100 | + |
| 2 | 100 | 100 | − |
| 3 | 100 | 100 | + |
| 4 | 100 | 100 | + |
| 5 | 100 | 100 | + |
| 6 | 89 | 100 | + |
| 7 | 0 | 100 | − |
| 8 | 100 | 100 | + |

TABLE II-continued

| Compound | Pesticidal[a] Activity TSM[b] | SAW[b] | Nema[c] |
|---|---|---|---|
| 9 | 0 | 100 | + |
| 10 | 100 | 100 | + |
| 11 | 100 | 100 | + |
| 12 | 100 | 100 | + |
| 13 | 100 | 100 | + |
| 14 | 100 | 100 | + |
| 15 | 100 | 100 | + |
| 16 | 100 | 100 | + |

[a]TSM = two-spotted mite SAW = southern armyworm Nema = nematode
[b]Screening test results, % control with 600 ppm spray solution.
[c]Screening test results, relative knotting at 30 ppm incorporated in soil "(+)" = 0-25 knots on root "(−)" = 25 knots on root For use as pesticides, the compounds of this invention can be used as solutions, suspensions, or mixtures, in organic solvents or formulations. For example, they can be formulated as wettable powders, emulsifiable concentrates, dusts, granular formulations or flowable emulsifiable concentrates. In such formulations, the compounds of this invention are present at a concentration of about 0.00001 to about 99%, preferably about 1 to about 95%, and are extended with an agronomically acceptable liquid or solid carrier. When desired, suitable surfactants are likewise incorporated. Surfactants commonly used in the art can be found in the John W. McCutcheon, Inc. publication "Detergents and Emulsifiers Annual."

By "agronomically acceptable carrier" is meant any substance which can be utilized to dissolve, disperse or diffuse the chemical incorporated therein without impairing the effectiveness of the toxic agent and which does not create permanent damage to such environment as soil, equipment, and agronomic crops when utilized according to recommendations.

The compounds of this invention can be taken up on or mixed with a finely particled solid carrier, as for example, clays, inorganic silicates, carbonates, and silicas. Organic carriers can also be employed.

Dust concentrates are commonly made wherein compounds are present in the range of about 20 to about 80%. For ultimate applications, these concentrates are normally extended with additional solid to give an active ingredient content of from 1 to about 20%. Granular formulations are being made using a granular or pelletized form of carrier, such as granular clays, vermiculite, charcoal or corn cobs, and may contain the active ingredient in from about 1 to about 25% by weight.

Wettable powder formulations are made by incorporating the compounds of this invention in an inert, finely divided solid carrier along with a surfactant which can be one or more emulsifying, wetting, dispersing, or spreading agents or a blend of these. The compounds are usually present in the range of about 10 to about 80% by weight and surfactants in from about 0.5 to about 10% by weight. Commonly used emulsifying and wetting agents include polyoxyethylated derivatives of alkylphenols, fatty alcohols, fatty acids, alkylamines, alkylarene sulfonates and dialkyl sulfosuccinates. Spreading agents include such materials as glycerol mannitan laurate and a condensate of polyglycerol and oleic acid modified with phthalic anhydride. Dispersing agents include such materials as the sodium salt of the copolymer of maleic anhydride and an olefin such as diisobutylene, sodium lignin sulfonate and sodium formaldehydenaphthalene sulfonates.

One convenient method for preparing a solid formulation is to impregnate the compounds of this invention onto the solid carrier by means of a volatile solvent, such as acetone. In this manner, adjuvants, such as activators, adhesives, plant nutrients, synergists and various surfactants can also be incorporated.

Emulsifiable concentrate formulations are prepared by dissolving the compounds of this invention in an agronomically acceptable organic solvent and adding a solvent-soluble emulsifying agent. Suitable solvents are usually water-immiscible and can be found in the hydrocarbon, chlorinated hydrocarbon, ketone, ester, alcohol and amide classes of organic solvents. Mixtures of solvents are commonly employed. The surfactants useful as emulsifying agents can constitute about 0.5 to about 10% by weight of emulsifiable concentrates and can be anionic, cationic or non-ionic in character. The concentration of the active ingredients can vary from about 10 to about 80%, preferably in the range of about 25 to about 50%.

For use as pesticidal agents, these compounds should be applied in an effective amount sufficient to exert the desired pesticidal activity by techniques well known in the art. In certain situations, however, it may be desirable and advantageous to apply the compounds directly onto the loci to be protected or freed of pests without the benefit of any substantial amount of carrier. This is a particularly effective method when the physical nature of the toxicants is such as to permit what is known as "low-volume" application, that is, when the compounds are in liquid form or substantially soluble in higher boiling solvents.

The application rate will, of course, vary depending upon the purpose for such application, the compound being utilized, the frequency of dissemination, and the like.

Many of the above formulations can be utilized on animals for the control of parasites.

For use as arthropodicides, e.g. acaricides and insecticides, dilute sprays can be applied at concentrations of about 0.01 to about 20 pounds of the active ingredients per 100 gallons of spray. They are usually applied at about 0.1 to about 5 pounds per 100 gallons. In more concentrated sprays, the active ingredient is increased by a factor of 2 to 40. With dilute sprays, applications are usually made to the plants until run-off is achieved, whereas with more concentrated or low-volume sprays, the materials are applied as mists.

For use as a nematocide or as a soil insecticide, the compounds can be applied as a dilute liquid preparation or as a solid formulation, preferably a granular formulation, by broadcasting, side-dressing, introduction into the seed furrow, soil incorporation, or seed treatment. The application rate can be from about 1 to about 50 pounds per acre of active ingredient and for economic reasons, preferably from about 1 to about 25 pounds per acre.

For use as a fungicide, the organophosphorothiolate or phosphorodithioate can be applied by methods commonly employed, such as conventional high-gallonage hydraulic sprays, low-gallonage sprays, air-blast sprays aerial sprays and dusts. The dilution and rate of application will depend upon the type of equipment employed, the method of application and diseases to be controlled, but the preferred effective amount is usually about 0.1 to about 50 pounds per acre of the active ingredient.

As a fungicidal seed protectant, the amount of toxicant coated on the seed is usually at a dosage rate of about 0.1 to about 20 ounces per hundred pounds of seed. As a soil fungicide the chemical can be incorporated in the soil or applied to the surface usually at a rate of about 0.1 to about 50 pounds per acre. As a foliar fungicide, the toxicant is usually applied to growing plants at a rate of about 0.25 to about 10 lbs. per acre.

The compounds of this invention can be utilized as the sole pesticidal agents or they can be employed in conjunction with other bactericides, fungicides, herbicides, insecticides, acaricides, and comparable pesticides.

Many variations of this invention are possible without departing from the spirit or scope thereof.

We claim:

1. A compound of the formula:

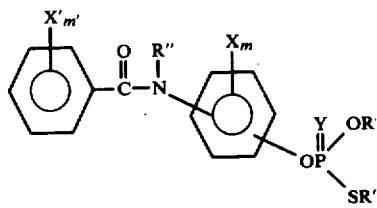

wherein
R is a $(C_1-C_4)$alkyl group;
R' is a $(C_3-C_6)$alkyl group;
R'' is a hydrogen atom, or a $(C_1-C_5)$alkyl group;
X is a halogen atom, a $(C_1-C_5)$alkyl group, or a $(C_1-C_5)$alkoxy group;
X' is a halogen atom, a nitro group, a cyano group, a $(C_1-C_5)$alkyl group, a $(C_1-C_5)$alkoxy group, or a $(C_1-C_5)$alkylthio group;
Y is an oxygen atom or a sulfur atom; and
m and m' are independently an integer from 0 to 3.

2. A method of controlling pests which comprises applying directly to the pests or to the loci to be freed of or protected from attack by such pests, a pesticidally effective amount of the compound of claim 1.

3. A compound according to claim 1 wherein R is a $(C_1-C_3)$alkyl group, R' is a $(C_3-C_5)$alkyl group of the formula:

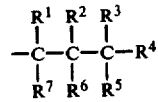

wherein
$R^1-R^7$ are individually hydrogen, methyl, or ethyl; and
R'' is a hydrogen atom, or a $(C_1-C_3)$alkyl group;

4. A compound according to claim 3 wherein
X is a halogen atom, a $(C_1-C_3)$alkyl group; or a $(C_1-C_3)$alkoxy group;
X' is a halogen atom, a $(C_1-C_3)$alkyl group, a $(C_1-C_3)$alkoxy group, or a $(C_1-C_3)$alkylthio group.

5. A compound according to claim 4 wherein Y is an oxygen atom.

6. A compound according to claim 5 wherein
R is a methyl group or an ethyl group;
R' is a $(C_3-C_4)$alkyl group;
R'' is a hydrogen atom, a methyl group or an ethyl group;
X is a chlorine atom, a methyl group, an ethyl group, a methoxy group, or an ethoxy group;
X' is a chlorine atom, a methyl group, a methoxy group, or a methylthio group.

7. A compound according to claim 6 wherein
R is an ethyl group;
R' is a n-propyl group, an isobutyl group, or a sec-butyl group;
R'' is a hydrogen atom; and
m is 0.

8. A compound according to claim 7 wherein X' is a chlorine atom and m' is an integer of 0 or 1.

9. A compound according to claim 8 having the formula:

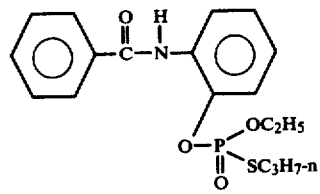

10. A compound according to claim 8 having the formula:

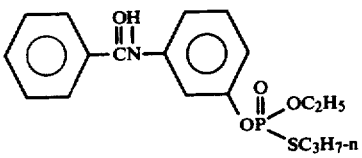

11. A compound according to claim 8 having the formula:

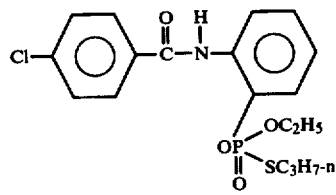

12. A compound according to claim 8 having the formula:

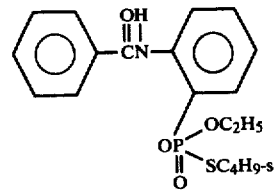

13. A pesticidal composition comprising a compound according to claim 1 and an agronomically acceptable carrier.

14. A method of controlling pests which comprises applying directly to the pests or to the loci to be freed of or protected from attack by such pests, a pesticidally effective amount of the composition of claim 13.

15. A method according to claim 14 wherein the pests are phytopathogenic fungi.

16. A method according to claim 14 wherein the pests are acarids.

17. A method according to claim 14 wherein the pests are insects.

18. A method according to claim 14 wherein the pests are nematodes.

* * * * *